(12) United States Patent
Gao et al.

(10) Patent No.: US 12,319,939 B2
(45) Date of Patent: Jun. 3, 2025

(54) CARBONYL REDUCTASE MUTANT AND ITS APPLICATION

(71) Applicant: Shandong University of Technology, Shandong (CN)

(72) Inventors: Xiuzhen Gao, Shandong (CN); Qinyuan Ma, Shandong (CN); Yanmiao Yin, Shandong (CN); Yanling Zhao, Shandong (CN); Zhixin Ma, Shandong (CN); Tong Zhang, Shandong (CN)

(73) Assignee: Shandong University of Technology, Zibo (CN)

( * ) Notice: Subject to any disclaimer, the term of this patent is extended or adjusted under 35 U.S.C. 154(b) by 0 days.

(21) Appl. No.: 18/933,327

(22) Filed: Oct. 31, 2024

(65) Prior Publication Data

US 2025/0145970 A1    May 8, 2025

(30) Foreign Application Priority Data

Nov. 3, 2023   (CN) .......................... 202311450405.0

(51) Int. Cl.
*C12N 9/04*   (2006.01)
*C12N 1/21*   (2006.01)
*C12P 7/62*   (2022.01)

(52) U.S. Cl.
CPC .............. *C12N 9/0006* (2013.01); *C12P 7/62* (2013.01); *C12Y 101/01184* (2013.01)

(58) Field of Classification Search
None
See application file for complete search history.

(56) References Cited

U.S. PATENT DOCUMENTS 10,294,479 B2 *   5/2019   Xu ........................... C12N 1/16
2018/0265875 A1   9/2018   Xu et al.

FOREIGN PATENT DOCUMENTS

| CN | 111593030 A | 8/2020 |
| CN | 115433721 A | 12/2022 |
| CN | 116814572 A | 9/2023 |
| WO | 2004028339 A2 | 4/2004 |

* cited by examiner

*Primary Examiner* — Todd M Epstein (57) ABSTRACT

The present disclosure relates to the technical field of biotechnology, in particular to carbonyl reductase mutant and its application. Specifically, the present disclosure provides a carbonyl reductase mutant for catalyzing the preparation of (R)-8-chloro-6-hydroxyoctanoic acid ethyl ester from 8-chloro-6-oxooctanoic acid ethyl ester. The mutant protein is a non natural protein and undergoes mutations in three core amino acids related to enzyme catalytic activity in the initial carbonyl reductase. The advantageous effect of the present disclosure is that the carbonyl reductase mutant provided by the present disclosure has the characteristic of efficiently catalyzing the preparation of the precursor substance (R)-8-chloro-6-hydroxyoctanoic acid from 8-chloro-6-oxooctanoic acid ethyl ester, and can efficiently catalyze the oxidation-reduction reaction of 8-chloro-6-oxooctanoic acid, with a product space-time yield of 99.9 g·L−1·h−1 or more.

6 Claims, 7 Drawing Sheets

Specification includes a Sequence Listing.

8-chloro-6-oxooctanoic acid ethyl ester     (R)-8-chloro-6-hydroxyoctanoic acid ethyl ester

```
                              SEQUENCE LISTING

Sequence total quantity: 12
SEQ ID NO: 1            moltype = AA   length = 334
FEATURE                 Location/Qualifiers
source                  1..334
                        mol_type = protein
                        note = Candida orthopsilosis Co 90-125
                        organism = unidentified
SEQUENCE: 1
MPVFISGATG FIAQHVIKEL LNDGFQVIGS VRSKAKGEYL SSLIKSKKFS YAVVPDIVAT    60
GAFDQVLQEN QDIDSFIHTA SPVDFQVSDV QTGLLDPAIE GTKNVLIAIE KYGKNVKNVV   120
VTSSTSAVRD SSGSRPSNSL LTEASWNEIT LEQGLKSARL GYSAAKTFAE KEVWKFAAEH   180
NGTFNITTVN PTYVFGPQAF EVQNKSQLND SAEYVNNIFK LKPNDDIPMF VGLFIDVRDV   240
AKAHVAAIKK PKEFNGQRLV LINSAWTNEL LAVIINKHFP NVDIPKGNIE KSDEELKKAD   300
LKWDNSKTKK LLGYSFIPIE KSVVDAVQQL LDTE                               334

SEQ ID NO: 2            moltype = DNA   length = 1005
FEATURE                 Location/Qualifiers
source                  1..1005
                        mol_type = other DNA
                        organism = unidentified
                        strain = Candida orthopsilosis Co 90-125
SEQUENCE: 2
atgccggttt tcatcagcgg cgcgaccggt ttcatcgcgc agcacgttat caaagaactg    60
ctgaacgatg gtttccaggt tatcggtagc gttcgttcta aagcgaaagg cgaatacctg   120
agcagcctga tcaaatctaa aaaattctct tacgcggttg ttccggatat cgttgcgacc   180
ggcgcgttcg atcaggttct gcaggaaaac caggatatcg atagcttcat ccacaccgct   240
tctccggttg atttccaggt tagcgatgtt cagaccggtc tgctggatcc ggcgatcgaa   300
ggtaccaaaa acgttctgat cgcgatcgaa aaatacggta aaaacgttaa aaacgttgtt   360
gttacctctt ccaccagcgc ggttcgtgac agcagcggta gccgtccgtc taacagcctg   420
ctgaccgaag cgagctggaa cgaaatcacc ctggaacagg gtctgaaatc tgcgcgtctg   480
ggctacagcg cggcgaaaac cttcgcagaa aagaagtgt ggaaattcgc ggcggaacac   540
aacggcacct tcaacatcac caccgttaac ccgacctacg ttttcggtcc gcaggcgttc   600
gaagttcaga acaaaagcca gctgaacgat tctgctgaat acgttaacaa catcttcaaa   660
ctgaaaccga acgatgatat cccgatgttc gttggcctgt tcatcgatgt gcgtgatgtt   720
gcgaaagcgc acgttgcggc gatcaaaaaa ccgaaagaat taacggcca gcgtctggtg   780
ctgatcaaca gcgcatggac caacgaactg ctggcggtta tcatcaacaa acacttcccg   840
aacgttgata tcccgaaagg caacatcgaa aaaagcgatg aagaactgaa aaaagcggat   900
ctgaaatggg ataactctaa aaccaaaaaa ctgctgggct acagcttcat cccgatcgaa   960
aaaagcgtgg ttgatgcggt tcagcagctg ctggataccg aataa                 1005

SEQ ID NO: 3            moltype = AA   length = 334
FEATURE                 Location/Qualifiers
source                  1..334
                        mol_type = protein
                        organism = synthetic construct
SEQUENCE: 3
MPVFISGATG FIAQHVIKEL LNDGFQVIGS VRSKAKGEYL SSLIKSKKFS YAVVPDIVAT    60
GAFDQVLQEN QDIDSFIHTA SPVDFQVSDV QTGLLDPAIE GTKNVLIAIE KYGKNVKNVV   120
VTSSTSAVLD SSGSRPSNSL LTEASWNEIT LEQGLKSARL GYSAAKTFAE KEVWKFAAEH   180
NGTFNITTVN PTYVFGPQAF EVQNKSQLNT SAEYVNNIFK LKPNDDIPMF VGLFIDVRDV   240
AKAHVAAIKK PKEFNGQRLV LINSAWTNEL LAVIINKHFP NVDIPKGNIE KSDEELKKAD   300
LKWDNSKTKK LLGYSFIPIE KSVVDAVQQL LDTE                               334

SEQ ID NO: 4            moltype = DNA   length = 1005
FEATURE                 Location/Qualifiers
source                  1..1005
                        mol_type = other DNA
                        organism = synthetic construct
SEQUENCE: 4
atgccggttt tcatcagcgg cgcgaccggt ttcatcgcgc agcacgttat caaagaactg    60
ctgaacgatg gtttccaggt tatcggtagc gttcgttcta aagcgaaagg cgaatacctg   120
agcagcctga tcaaatctaa aaaattctct tacgcggttg ttccggatat cgttgcgacc   180
ggcgcgttcg atcaggttct gcaggaaaac caggatatcg atagcttcat ccacaccgct   240
tctccggttg atttccaggt tagcgatgtt cagaccggtc tgctggatcc ggcgatcgaa   300
ggtaccaaaa acgttctgat cgcgatcgaa aaatacggta aaaacgttaa aaacgttgtt   360
gttacctctt ccaccagcgc ggttctggac agcagcggta gccgtccgtc taacagcctg   420
ctgaccgaag cgagctggaa cgaaatcacc ctggaacagg gtctgaaatc tgcgcgtctg   480
ggctacagcg cggcgaaaac cttcgcagaa aagaagtgt ggaaattcgc ggcggaacac   540
aacggcacct tcaacatcac caccgttaac ccgacctacg ttttcggtcc gcaggcgttc   600
gaagttcaga acaaaagcca gctgaacacc tctgctgaat acgttaacaa catcttcaaa   660
ctgaaaccga acgatgatat cccgatgttc gttggcctgt tcatcgatgt gcgtgatgtt   720
gcgaaagcgc acgttgcggc gatcaaaaaa ccgaaagaat taacggcca gcgtctggtg   780
ctgatcaaca gcgcatggac caacgaactg ctggcggtta tcatcaacaa acacttcccg   840
```

```
aacgttgata tcccgaaagg caacatcgaa aaaagcgatg aagaactgaa aaaagcggat    900
ctgaaatggg ataactctaa aaccaaaaaa ctgctgggct acagcttcat cccgatcgaa    960
aaaagcgtgg ttgatgcggt tcagcagctg ctggataccg aataa                   1005

SEQ ID NO: 5          moltype = AA   length = 334
FEATURE               Location/Qualifiers
source                1..334
                      mol_type = protein
                      organism = synthetic construct
SEQUENCE: 5
MPVFISGATG FIAQHVIKEL LNDGFQVIGS VRSKAKGEYL SSLIKSKKFS YAVVPDIVAT     60
GAFDQVLQEN QDIDSFIHTA SPVDFQVSDV QTGLLDPAIE GTKNVLIAIE KYGKNVKNVV    120
VTSSTAAVLD SSGSRPSNSL LTEASWNEIT LEQGLKSARL GYSAAKTFAE KEVWKFAAEH    180
NGTFNITTVN PTYVFGPQAF EVQNKSQLNT SAEYVNNIFK LKPNDDIPMF VGLFIDVRDV    240
AKAHVAAIKK PKEFNGQRLV LINSAWTNEL LAVIINKHFP NVDIPKGNIE KSDEELKKAD    300
LKWDNSKTKK LLGYSFIPIE KSVVDAVQQL LDTE                                334

SEQ ID NO: 6          moltype = DNA   length = 1005
FEATURE               Location/Qualifiers
source                1..1005
                      mol_type = other DNA
                      organism = synthetic construct
SEQUENCE: 6
atgccggttt tcatcagcgg cgcgaccggt ttcatcgcgc agcacgttat caaagaactg     60
ctgaacgatg gtttccaggt tatcggtagc gttcgttcta agcgaaagg cgaatacctg    120
agcagcctga tcaaatctaa aaaattctct tacgcggttg ttccggatat cgttgcgacc    180
ggcgcgttcg atcaggttct gcaggaaaac caggatatcg atagcttcat ccacaccgct    240
tctccggttg atttccaggt tagcgatgtt cagaccggtc tgctggatcc ggcgatcgaa    300
ggtaccaaaa acgttctgat cgcgatcgaa aaatacggta aaaacgttaa aaacgttgtt    360
gttacctctt ccaccgcggc ggttctggac agcagcggtc gccgtccgtc taacagcctg    420
ctgaccgaag cgagctggaa cgaaatcacc ctggaacagg gtctgaaatc tgcgcgtctg    480
ggctacagcg cggcgaaaac cttcgcagaa aaagaagtgt ggaaattcgc ggcggaacac    540
aacggcacct tcaacatcac caccgttaac ccgacctacg ttttcggtcc gcaggcgttc    600
gaagttcaga acaaaagcca gctgaacacc tctgctgaat acgttaacaa catcttcaaa    660
ctgaaaccga acgatgatat cccgatgttc gttggcctgt tcatcgatgt gcgtgatgtt    720
gcgaaagcgc acgttgcggc gatcaaaaaa ccgaaagaat taacggcca gcgtctggtg    780
ctgatcaaca gcgcatggac caacgaactg ctggcggtta tcatcaacaa acacttcccg    840
aacgttgata tcccgaaagg caacatcgaa aaaagcgatg aagaactgaa aaaagcggat    900
ctgaaatggg ataactctaa aaccaaaaaa ctgctgggct acagcttcat cccgatcgaa    960
aaaagcgtgg ttgatgcggt tcagcagctg ctggataccg aataa                   1005

SEQ ID NO: 7          moltype = DNA   length = 30
FEATURE               Location/Qualifiers
source                1..30
                      mol_type = other DNA
                      organism = synthetic construct
SEQUENCE: 7
tccaccagcg cggttctgga cagcagcggt                                      30

SEQ ID NO: 8          moltype = DNA   length = 30
FEATURE               Location/Qualifiers
source                1..30
                      mol_type = other DNA
                      organism = synthetic construct
SEQUENCE: 8
gctaccgctg ctgtccagaa ccgcgctggt                                      30

SEQ ID NO: 9          moltype = DNA   length = 30
FEATURE               Location/Qualifiers
source                1..30
                      mol_type = other DNA
                      organism = synthetic construct
SEQUENCE: 9
aaaagccagc tgaacacctc tgctgaatac                                      30

SEQ ID NO: 10         moltype = DNA   length = 30
FEATURE               Location/Qualifiers
source                1..30
                      mol_type = other DNA
                      organism = synthetic construct
SEQUENCE: 10
aacgtattca gcagaggtgt tcagctggct                                      30

SEQ ID NO: 11         moltype = DNA   length = 30
FEATURE               Location/Qualifiers
source                1..30
                      mol_type = other DNA
                      organism = synthetic construct
SEQUENCE: 11
```

```
gttacctctt ccaccgcggc ggttctggac                                  30

SEQ ID NO: 12           moltype = DNA   length = 30
FEATURE                 Location/Qualifiers
source                  1..30
                        mol_type = other DNA
                        organism = synthetic construct
SEQUENCE: 12
gctgtccaga accgccgcgg tggaagaggt                                  30
```

CARBONYL REDUCTASE MUTANT AND ITS APPLICATION

CROSS-REFERENCE

This application claims to the benefit of priority from Chinese Application No. 202311450405.0 with a filing date of Nov. 3, 2023. The content of the aforementioned applications, including any intervening amendments thereto, are incorporated herein by reference.

SEQUENCE LISTING

The instant application contains a Sequence Listing with 12 sequence, which has been submitted electronically in XML format and is hereby incorporated herein by reference in its entirety. Said XML copy, created on Oct. 30, 2024, is named QDZJ-US-1-22-Sequence Listings.xml, and is 16 kbytes in size.

TECHNICAL FIELD

The present disclosure relates to the technical field of bioengineering, in particular to a carbonyl reductase mutant and its application in the preparation of precursors of lipoic acid.

BACKGROUND

As a universal antioxidant, lipoic acid has obvious effects on the treatment of diabetes and other diseases, and has high application value in the industries such as medicine, cosmetics and etc., but only R-configuration has physiological activity. The current standards for the use of medicines and health products in various countries around the world have been raised, and the demand for (R)-lipoic acid synthesis technology from enterprises is gradually increasing, in order to change the current market model of mainly circulating in the form of lipoic acid racemate. In 2015, Xu Jianhe et al. (Y. J. Zhang, W. X. Zhang, G. W. Zheng, J. H. Xu, Advanced Synthesis&Catalysis. 2015, 357, 1697-1702.) proposed a competitive synthetic route using 8-chloro-6-oxo-octanoic acid ethyl ester as raw material, catalyzed by biological enzymes to synthesize (R)-8-chloro-6-hydroxyoctanoic acid ethyl ester, and then combined with subsequent chemical reactions to synthesize (R)-α-lipoic acid (the process route is shown in FIG. 1).

However, currently only two carbonyl reductases can be used to prepare high-purity (R)-8-chloro-6-hydroxyoctanoic acid ethyl ester. If a biological enzyme with stronger catalytic ability can be developed for the production of (R)-α-lipoic acid precursor, it will greatly improve the efficiency of industrial preparation of lipoic acid, which is of great significance for the development of the (R)-α-lipoic acid market.

SUMMARY

In order to prepare the precursor substance (R)-8-chloro-6-hydroxyoctanoic acid ethyl ester from 8-chloro-6-oxooctanoic acid ethyl ester as raw material, the present disclosure has developed a carbonyl reductase mutant that can efficiently catalyze the reaction of 8-chloro-6-oxooctanoic acid ethyl ester to prepare (R)-8-chloro-6-hydroxyoctanoic acid ethyl ester.

The carbonyl reductase mutant provided by the present disclosure has one of the following amino acid sequences selected for its protein:

(1) Replace arginine at position 129 with leucine and aspartic acid at position 210 with threonine in the amino acid sequence shown in SEQ ID No: 3;

(2) Replace arginine at position 129 with leucine, aspartic acid at position 210 with threonine, and serine at position 126 with alanine in the amino acid sequence shown in SEQ ID No: 5.

The nucleotide sequence of the coding gene for the carbonyl reductase mutant is shown in SEQ ID NO: 4 and SEQ ID: 6.

In addition, the present disclosure also provides a method for preparing the above-mentioned carbonyl reductase mutant, including the following steps: synthesizing a coding gene of an initial carbonyl reductase, conducting site directed mutagenesis of the coding gene of the initial carbonyl reductase, constructing an expression vector, transforming a protein expression host bacterium, and inducing protein expression.

The present disclosure starts with the substrate channel of the carbonyl reductase protein structure of *Candida orthopsilosis* Co 90-125 (amino acid sequence as shown in SEQ ID NO: 1) with ID XP 003867714.1 in Genbank, analyzes the entrance segment and internal structural characteristics of the substrate channel, and performs iterative saturation mutagenesisit through semi-rational design, so as to determine that the key factor affecting the initial enzymatic properties of carbonyl reductase is the amino acids at positions R129, D210 and S126. Then, the arginine (Arg) at position 129 is replaced with leucine (Leu) through codon substitution, aspartate (Asp) at position 210 is replaced with threonine (Thr), to obtain the highly active carbonyl reductase mutant target gene R129L/D210T (amino acid sequence as shown in SEQ ID NO: 3). On this basis, serine (Ser) at position 126 is replaced with alanine (Ala), to obtain the triple mutant R129L/D210T/S126A (amino acid sequence as shown in SEQ ID NO: 5).

Furthermore, the present disclosure also utilized molecular cloning technology to obtain the coding genes of the double mutant (SEQ ID NO: 4) and the triple mutant R129L/D210T/S126A (SEQ ID NO: 6). By constructing a 6× His fusion expression vector of the mutant genes and inducing expression in the genetically engineered bacterium *E. coli* Over Express C43 (DE3), two mutant enzyme proteins were obtained. The mutant was used as a catalyst and 8-chloro-6-oxooctanoic acid ethyl ester was used as a substrate for enzymatic reaction under appropriate conditions. The results showed that the ee value of (R)-8-chloro-6-hydroxyoctanoic acid ethyl ester synthesized by the double mutant and triple mutant increased to >99.5% compared to 86.44±5.41% of the initial enzyme, and the catalytic efficiency increased by 31.65 times and 93.42 times, respectively, compared to the initial carbonyl reductase. In the amplification reaction (50 mL), the space-time yield reached 99.9 g·L−1·h−1, which has great potential and value in the industrial production of (R)-lipoic acid.

The gene encoding carbonyl reductase mutants and the nucleotide sequences SEQ ID NO: 4 and SEQ ID NO: 6 of the gene mentioned above are the key protected contents of the present disclosure. In addition, gene expression cassettes, vectors, or recombinant bacteria containing the aforementioned gene also fall within the technical scope protected by the present disclosure.

Similarly, a catalyst containing the aforementioned carbonyl reductase mutant are also protected by the present disclosure.

Furthermore, the present disclosure also provides the application of the carbonyl reductase mutant or the catalyst containing the carbonyl reductase mutant in the reaction of 8-chloro-6-oxooctanoic acid ethyl ester.

The specific application is: using the carbonyl reductase mutant mentioned above or a catalyst containing the carbonyl reductase mutant mentioned above, catalyzing the reaction with 8-chloro-6-oxooctanoic acid ethyl ester as the substrate to synthesize the precursor of lipoic acid (R)-8-chloro-6-hydroxyoctanoic acid ethyl ester.

Furthermore, the above catalytic reaction is carried out under the conditions of 25-30° C., pH=7.0-7.5, and the concentration of 8-chloro-6-oxooctanoic acid ethyl ester of 33.3 g/L.

The advantageous effects of the present disclosure are as following:

Through the modification of carbonyl reductase, the efficient catalysis is achieved for the production of (R)-α-lipoic acid precursor, i.e. (R)-8-chloro-6-hydroxyoctanoic acid ethyl ester, using 8-chloro-6-oxooctanoic acid ethyl ester as raw material, which will significantly improve the production efficiency of (R)-α-lipoic acid precursor.

BRIEF DESCRIPTION OF THE DRAWINGS

FIG. 1 is a schematic diagram of enzymatic synthesis of (R)-8-chloro-6-hydroxyoctanoic acid ethyl ester;

FIG. 2 is the gas chromatogram of the catalytic product catalyzed by carbonyl reductase mutant R129L/D210T in a 2 mL reaction;

FIG. 3 is the gas chromatogram of the catalytic product catalyzed by carbonyl reductase mutant R129L/D210T/S126A in a 2 mL reaction;

FIG. 4 is the gas chromatogram of the catalytic product catalyzed by carbonyl reductase mutant R129L/D210T/S126A in a 50 mL reaction;

FIG. 5 is the high-performance liquid chromatography of the synthesis of different configuration products catalyzed by carbonyl reductase mutant R129L/D210T in a 2 mL reaction;

FIG. 6 is the high-performance liquid chromatography of the synthesis of different configuration products catalyzed by carbonyl reductase mutant R129L/D210T/S126A in a 2 mL reaction;

FIG. 7 is the high-performance liquid chromatography of the synthesis of different configuration products catalyzed by the carbonyl reductase mutant R129L/D210T/S126A in a 50 mL reaction.

DETAILED DESCRIPTION OF THE EMBODIMENTS

In order to enable skilled person in the art to better understand the present disclosure, the present disclosure will be further elaborated in conjunction with specific embodiments.

The present disclosure will be further described in conjunction with specific embodiments. It should be noted that the following embodiments are only for explanation and illustration, and do not limit the scope of the present disclosure in any way.

Main reagents and consumable materials: Phanta® Max Super-Fidelity DNA polymerase P505 was purchased from Nanjing Vazyme Biotech Co., Ltd.; FastDigest DpnI DNA endonuclease (item number: FD1703) was purchased from Thermo Fisher Scientific; The pET28 (a) plasmid is a known E. coli expression vector with a size of 5369 bp, T7 promoter, vector labels N-6× His and C-6× His, and resistance to Kanamycin, which were purchased from Novogen; E. coli DH5a competent cells (item number: G6016), E. coli Rosetta (DE3) competent cells (item number: G6031), and E. coli Overexpress C43 (DE3) competent cells (item number: X17016) were all purchased from Angyu Biotechnology Co., Ltd; Agar powder (item number: A8190), purchased from Solarbio; TRYPTONE (item number: LP0042) and YEAST EXTRACT (item number: LP0021) were both purchased from OXOID; and reagents such as NaCl (item number: 10019318), $K_2HPO_4 \cdot 3H_2O$ (item number: 10017518), $KH_2PO_4$ (item number: 10017618), and glycerol (item number: 10010618) were purchased from Sinopharm Chemical Reagent Co., Ltd.

LB Medium

Each 100 mL LB medium contains: 1 g tryptone, 0.5 g yeast extract, and 1 g NaCl, pH=7.0-7.2.

Preparation method: Dissolve 10 g of tryptone, 5 g of yeast extract, and 10 g of NaCl in 1 L of distilled water without adjusting the pH value; perform sterilization with high-pressure steam at 121° C. for 20 minutes. If preparing solid culture medium, add 1.8 g of agar powder to 100 mL culture medium.

Unless otherwise specified, the reagents used in the following embodiments are conventional reagents in this field, which can be purchased commercially or prepared according to conventional methods in this field, and the specifications are LR (Laboratory reagent). Unless otherwise specified, the methods used in the following embodiments are conventional methods in this field, and the experimental conditions used are routine in this field and can be referred to the relevant laboratory manuals or manufacturer's instructions.

Embodiment 1, Preparation of Carbonyl Reductase Mutant

1. Design of Carbonyl Reductase Mutant

Through gene mining, the carbonyl reductase gene with Genbank ID XP_003867714.1 was screened from the NCBI database. The open reading frame of this gene is 1005 bp long, the carbonyl reductase encoded by it consists of 334 amino acids, and its amino acid sequence (334aa) is:

```
                                       (SEQ ID NO: 1)
MPVFISGATGFIAQHVIKELLNDGFQVIGSVRSKAKGEYLSSLIKSKKFS

YAVVPDIVATGAFDQVLQENQDIDSFIHTASPVDFQVSDVQTGLLDPAIE

GTKNVLIAIEKYGKNVKNVVVTSSTSAVRDSSGSRPSNSLLTEASWNEIT

LEQGLKSARLGYSAAKTFAEKEVWKFAAEHNGTFNITTVNPTYVFGPQAF

EVQNKSQLNDSAEYVNNIFKLKPNDDIPMFVGLFIDVRDVAKAHVAAIKK

PKEFNGQRLVLINSAWTNELLAVIINKHFPNVDIPKGNIEKSDEELKKAD

LKWDNSKTKKLLGYSFIPIEKSVVDAVQQLLDTE.

The nucleotide sequence encoding the carbonyl
reductase is:
                                       (SEQ ID NO: 2)
atgccggttttcatcagcggcgcgaccggtttcatcgcgcagcacgttat caaagaactgctgaacgatggtttccaggttatcggtagcgttcgttcta aagcgaaaggcgaatacctgagcagcctgatcaaatctaaaaaattctct
```

```
tacgcggttgttccggatatcgttgcgaccggcgcgttcgatcaggttct gcaggaaaaccaggatatcgatagcttcatccacaccgcttctccggttg atttccaggttagcgatgttcagaccggtctgctggatccggcgatcgaa ggtaccaaaaacgttctgatcgcgatcgaaaaatacggtaaaaacgttaa aaacgttgttgttacctcttccaccagcgcggttcgtgacagcagcggta gccgtccgtctaacagcctgctgaccgaagcgagctggaacgaaatcacc ctggaacagggtctgaaatctgcgcgtctgggctacagcgcggcgaaaac cttcgcagaaaaagaagtgtggaaattcgcggcggaacacaacggcacct tcaacatcaccaccgttaacccgacctacgttttcggtccgcaggcgttc gaagttcagaacaaaagccagctgaacgattctgctgaatacgttaacaa catcttcaaactgaaaccgaacgatgatatcccgatgttcgttggcctgt tcatcgatgtgcgtgatgttgcgaaagcgcacgttgcggcgatcaaaaaa ccgaaagaatttaacggccagcgtctggtgctgatcaacagcgcatggac caacgaactgctggcggttatcatcaacaaacacttcccgaacgttgata tcccgaaaggcaacatcgaaaaagcgatgaagaactgaaaaaagcggat ctgaaatgggataactctaaaaccaaaaaactgctgggctacagcttcat cccgatcgaaaaagcgtggttgatgcggttcagcagctgctggataccg aataa.
```

The present disclosure analyzes the protein three-dimensional structure of the carbonyl reductase and determines that the key factor affecting the enzymatic properties of the initial carbonyl reductase is substrate channel steric hindrance. By selecting mutation sites at the entrance and channel inside of substrate channel, the key roles of R129, D210, and S126 sites were determined using an iterative saturation mutagenesis, wherein R129L/D210T and R129L/D210T/S126A mutants show good catalytic performance and enzyme activity.

The nucleotide sequence corresponding to R129 is codons 385-387, the nucleotide sequence corresponding to D210 is codons 628-630, and The nucleotide sequence corresponding to S126 is codons 376-378.

The double mutation R129L/D210T changed the codons 385-387 of the carbonyl reductase gene sequence from CGT to CTG, thereby replacing the 129th position of the amino acid sequence from arginine (R) to leucine (L); changed the codons 628-630th position from GAT to ACC, thereby the 210th position of the amino acid sequence from aspartic acid (D) to threonine (T), to obtain an enzyme mutant, wherein its amino acid sequence is shown in SEQ ID NO: 3, and the nucleotide sequence of the coding gene is shown in SEQ ID NO: 4.

While the triple mutation changed from AGC to GCG at codons 376-378 of the carbonyl reductase double mutant gene sequence, thereby replacing serine(S) with alanine (A) at position 126 of the amino acid sequence, to obtain a triple mutant, wherein its amino acid sequence is shown in SEQ ID NO: 5, and the nucleotide sequence of the coding gene is shown in SEQ ID NO: 6.

(SEQ ID NO: 3)
MPVFISGATGFIAQHVIKELLNDGFQVIGSVRSKAKGEYLSSLIKSKKFS

YAVVPDIVATGAFDQVLQENQDIDSFIHTASPVDFQVSDVQTGLLDPAIE

GTKNVLIAIEKYGKNVKNVVVTSSTSAVLDSSGSRPSNSLLTEASWNEIT

LEQGLKSARLGYSAAKTFAEKEVWKFAAEHNGTFNITTVNPTYVFGPQAF

EVQNKSQLNTSAEYVNNIFKLKPNDDIPMFVGLFIDVRDVAKAHVAAIKK

PKEFNGQRLVLINSAWTNELLAVIINKHFPNVDIPKGNIEKSDEELKKAD

LKWDNSKTKKLLGYSFIPIEKSVVDAVQQLLDTE.

(SEQ ID NO: 4)
atgccggttttcatcagcggcgcgaccggtttcatcgcgcagcacgttat caaagaactgctgaacgatggtttccaggttatcggtagcgttcgttcta aagcgaaaggcgaatacctgagcagcctgatcaaatctaaaaaattctct tacgcggttgttccggatatcgttgcgaccggcgcgttcgatcaggttct gcaggaaaaccaggatatcgatagcttcatccacaccgcttctccggttg atttccaggttagcgatgttcagaccggtctgctggatccggcgatcgaa ggtaccaaaaacgttctgatcgcgatcgaaaaatacggtaaaaacgttaa aaacgttgttgttacctcttccaccagcgcggttctggacagcagcggta gccgtccgtctaacagcctgctgaccgaagcgagctggaacgaaatcacc ctggaacagggtctgaaatctgcgcgtctgggctacagcgcggcgaaaac cttcgcagaaaaagaagtgtggaaattcgcggcggaacacaacggcacct tcaacatcaccaccgttaacccgacctacgttttcggtccgcaggcgttc gaagttcagaacaaaagccagctgaacacctctgctgaatacgttaacaa catcttcaaactgaaaccgaacgatgatatcccgatgttcgttggcctgt tcatcgatgtgcgtgatgttgcgaaagcgcacgttgcggcgatcaaaaaa ccgaaagaatttaacggccagcgtctggtgctgatcaacagcgcatggac caacgaactgctggcggttatcatcaacaaacacttcccgaacgttgata tcccgaaaggcaacatcgaaaaagcgatgaagaactgaaaaaagcggat ctgaaatgggataactctaaaaccaaaaaactgctgggctacagcttcat cccgatcgaaaaagcgtggttgatgcggttcagcagctgctggataccg aataa.

(SEQ ID NO: 5)
MPVFISGATGFIAQHVIKELLNDGFQVIGSVRSKAKGEYLSSLIKSKKFS

YAVVPDIVATGAFDQVLQENQDIDSFIHTASPVDFQVSDVQTGLLDPAIE

GTKNVLIAIEKYGKNVKNVVVTSSTAAVLDSSGSRPSNSLLTEASWNEIT

LEQGLKSARLGYSAAKTFAEKEVWKFAAEHNGTFNITTVNPTYVFGPQAF

EVQNKSQLNTSAEYVNNIFKLKPNDDIPMFVGLFIDVRDVAKAHVAAIKK

PKEFNGQRLVLINSAWTNELLAVIINKHFPNVDIPKGNIEKSDEELKKAD

LKWDNSKTKKLLGYSFIPIEKSVVDAVQQLLDTE.

(SEQ ID NO: 6)
atgccggttttcatcagcggcgcgaccggtttcatcgcgcagcacgttat caaagaactgctgaacgatggtttccaggttatcggtagcgttcgttcta -continued

```
aagcgaaaggcgaatacctgagcagcctgatcaaatctaaaaaattctct tacgcggttgttccggatatcgttgcgaccggcgcgttcgatcaggttct gcaggaaaaccaggatatcgatagcttcatccacaccgcttctccggttg atttccaggttagcgatgttcagaccggtctgctggatccggcgatcgaa ggtaccaaaaacgttctgatcgcgatcgaaaaatacggtaaaaacgttaa aaacgttgttgttacctcttccaccgcggcggttctggacagcagcggta gccgtccgtctaacagcctgctgaccgaagcgagctggaacgaaatcacc ctggaacagggtctgaaatctgcgcgtctgggctacagcgcggcgaaaac cttcgcagaaaagaagtgtggaaattcgcggcggaacacaacggcacct tcaacatcaccaccgttaacccgacctacgttttcggtccgcaggcgttc gaagttcagaacaaaagccagctgaacacctctgctgaatacgttaacaa catcttcaaactgaaaccgaacgatgatatcccgatgttcgttggcctgt tcatcgatgtgcgtgatgttgcgaaagcgcacgttgcggcgatcaaaaaa ccgaaagaatttaacggccagcgtctggtgctgatcaacagcgcatggac caacgaactgctggcggttatcatcaacaaacacttcccgaacgttgata tcccgaaaggcaacatcgaaaaaagcgatgaagaactgaaaaaagcggat ctgaaatgggataactctaaaaccaaaaaactgctgggctacagcttcat cccgatcgaaaaagcgtggttgatgcggttcagcagctgctggataccg aataa.
```

2. Obtainment of Carbonyl Reductase Mutant Gene

The carbonyl reductase mutant gene can be obtained through whole gene synthesis or molecular cloning methods. This experiment used whole gene synthesis method to obtain the carbonyl reductase gene with Genbank ID XP_003867714.1, and PCR method to obtain the carbonyl reductase mutant gene.

1. Whole Gene Synthesis of Initial Carbonyl Reductase

Whole gene synthesis was performed on carbonyl reductase with Genbank ID XP_003867714.1, and the synthesized gene fragment was ligated into the pET28A (+) plasmid. Sangon Biotech (Shanghai) Co., Ltd. was trusted to synthesize the above-mentioned genes.

2. Site Directed Mutagenesis of Carbonyl Reductase (1) Primer Design for Site Directed Mutagenesis (2) Site Directed Mutagenesis of Carbonyl Reductase Using the pET28A (+) plasmid containing the initial carbonyl reductase gene as a template, the carbonyl reductase mutant gene was amplified using the upstream and downstream primers obtained in step (1) according to the following PCR system and procedure.

The PCR system: Phanta® Max Super-Fidelity DNA polymerase P505 0.5 μL, template plasmid 0.6 μL, upstream primer-F (10 μM) 1 μL, downstream primer-R (10 μM) 1 μL, 2×PCR Buffer 12.5 μL, dNTP mix 0.5 μL, and ddH$_2$O 8.9 μL.

The PCR procedure is as follows: a. perform pre-denaturation at 95° C. for 5 minutes; b. perform denaturation at 95° C. for 30 seconds, anneal at 55° C. for 30 seconds, extend at 72° C. for 3.75 minutes, 20 cycles; c. extend at 72° C. for 10 minutes, cool down to 4° C., use DpnI enzyme to digest the template plasmid containing the initial carbonyl reductase gene at 37° C. for 30 minutes.

(3) Transformation of DH5α Competent Cell

Transform the digestion product of pET28A (+) plasmid containing carbonyl reductase mutant obtained in step (2) into DH5α competent cells.

Place DH5α competent cells on ice, wait for the cells to melt, add 15 μL plasmid solution, let it sit on ice for 30 minutes; heat shock at 42° C. for 45 seconds, then let it stand on ice for 2 minutes; add 700 μL sterile LB liquid medium, culture at 37° C. and 200 rpm in a shaker for 1 hour, centrifuge at 4000 rpm for 1 minute, and leave 200 μL supernatant; mix the precipitated bacterial cells with the supernatant, then coat them all onto LB plate medium containing Kana resistance (50 u g/mL), and then inverted and culture overnight at 37° C.

(4) Positive Clone Screening

Select single colony from LB agar plates and inoculate them into LB liquid medium containing Kana resistance (50 μg/mL), incubate overnight at 37° C. and 200 rpm on a shaker; after preservation (sterile glycerol final concentration of 15%), send them to GENEWIZ (Suzhou, China) company for sequencing to identify whether the initial carbonyl reductase mutation is successful. The plasmid is required to return from the company when the sequencing is successful.

3. Heterologous Expression of Carbonyl Reductase Mutant 6× his Fusion Protein (1) Protein Expression Competent Cells Transformation Take out Overexpress C43 (DE3) competent cells from a −80° C. ultra-low temperature refrigerator, place them on ice, and add 1 μL of pET28A (+) plasmid containing carbonyl reductase mutant to each competent cell after the cells melt, place them on ice for 30 minutes, heat shock at 42° C. for 45 seconds, then place them on ice for 2 minutes,

TABLE 1

Mutant Primer Design

| Primer | Sequence name | Sequence (5'-3') | Template |
|---|---|---|---|
| R129L-F | SEQ ID NO: 7 | tccaccagcgcggttctggacagcagcggt | CoCR 13 |
| R129L-R | SEQ ID NO: 8 | gctaccgctgctgtccagaaccgcgctggt | |
| D210T-F | SEQ ID NO: 9 | aaaagccagctgaacacctctgctgaatac | R129L |
| D210T-R | SEQ ID NO: 10 | aacgtattcagcagaggtgttcagctggct | |
| S126A-F | SEQ ID NO: 11 | gttacctcttccaccgcggcggttctggac | R129L/ |
| S126A-R | SEQ ID NO: 12 | gctgtccagaaccgccgcggtggaagaggt | D210T | add 700 μL sterile LB liquid culture medium, culture at 37° C. and 200 rpm for 1 hour in a shaker, take 200 μL of cultured bacterial solution, apply it to LB plate medium containing Kana resistance (50 μg/mL), and inverted and culture overnight at 37° C.

(2) Preservation of Carbonyl Reductase Mutant Expression Strain

Select single colony from LB plate and inoculate them into test tubes of LB liquid medium containing Kana resistant (50 µg/mL), incubate overnight at 37° C. and 200 rpm on a shaker as an expression strain for carbonyl reductase mutants; add sterile glycerol with a final volume concentration of 15% to the bacterial solution and store it in a −80° C. ultra-low temperature freezer for long term preservation.

(3) Protein Expression

Transfer the overnight cultured test tube bacterial solution into 50 mL of sterile LB liquid culture medium (inoculation volume of 1%), with a final concentration of kanamycin of 50 µg/mL, cultured at 37° C. and 200 rpm for about 2.5 hours. When $OD_{600}$=0.6-0.8, add sterile IPTG with a final concentration of 0.1 mM, induce and culture at 28° C. and 200 rpm for 6 hours, then centrifuge at 8000 rpm for 10 minutes, and collect the bacterial cells.

Embodiment 2, Determination of Enzyme Activity and Kinetic Parameters of Carbonyl Reductase CoCR 13 and its Mutants (1) Enzyme Activity Assay The carbonyl reductase enzyme activity assay system is as follows: 150 µL PB buffer (100 mM, pH 7.0), 10 µL NADPH (0.25 g/L), 20 µL 8-chloro-6-oxooctanoic acid ethyl ester (2.5 mM, dissolved in DMF), 20 µL purified mutant enzyme solution, and the mixed system is added to a 96-well plate; measure the decrease in light absorption value at 340 nm within 6 minutes at 30° C. using a microplate reader, and calculate the amount of NADPH consumed by the reaction based on the standard curve.

One enzyme activity unit U is defined as the amount of enzyme required to consume 1 µmol NADPH within 1 minute.

(3) Kinetic Parameters

The substrate concentration was set to be 0.1-10 mM, and the rest was the same enzyme activity determination system and reaction conditions as described above.

Conclusion: The carbonyl reductase mutants with amino acid sequences such as SEQIDNO: 3 and SEQIDNO: 5 exhibit higher catalytic reduction activity and efficiency towards 8-chloro-6-oxooctanoic acid ethyl ester compared to the wild-type carbonyl reductase.

The enzyme activity was determined at different temperatures using the enzyme activity at 30° C. as the standard of 100%.

The optimal temperature for the wild-type is 30° C., while the optimal temperature for the three mutants R129L/D210T/S126A is 30° C.

(2) Optimal pH

In Embodiment 2, the buffer was replaced with citric acid-citrate buffer system (pH 4.0-6.0), phosphate buffer system (pH 6.0-8.0), and Tris-HCl buffer system (pH 8.0-9.0) to measure enzyme activity, with PB (pH 7.0) enzyme activity as the standard of 100%.

Result: The optimal pH for CoCR 13 is 7.0, and the optimal pH for R129L/D210T/S126A is 7.5.

Embodiment 4, Synthesis and Detection of 8-Chloro-6-Hydroxyoctanoic Acid Ethyl Ester Using Carbonyl Reductase Mutant 1. Synthesis of 8-chloro-6-hydroxyoctanoic acid ethyl ester (1) 2 mL reaction system: Take 200 mM PB (pH 7.0), carbonyl reductase CoCR 13 or the double mutant R129L/D210T or triple mutant R129L/D210T/S126A 50 g/L from Embodiment 1, GDH 25 g/L stored in the laboratory, 150 mM 8-chloro-6-oxooctanoate acid ethyl ester, 225 mM glucose, 0.25 g/L NADP+, and 1.5% DMF into a 5 mL EP tube for reaction overnight at 30° C. and 250 rpm overnight; 2 mL of ethyl acetate was added to the reaction solution for full extraction, then centrifuge at 6000 rpm for 5 minutes to collect the supernatant for detection.

(2) 50 mL reaction system: Take 200 mM PBS (pH 7.5), 20 g/L of carbonyl reductase mutant R129L/D210T/S126A from Embodiment 1, 10 g/L of GDH stored in the laboratory, 150 mM 8-chloro-6-oxooctanoic acid ethyl ester, 225 mM glucose, 0.1 g/L NADP+, and 1.5% DMF into a 250 mL reaction vessel for reaction at 30° C. and 500 rpm for 20 minutes. The reaction mixture was fully extracted with the same volume of ethyl acetate and centrifuged at 6000 rpm for 5 minutes to obtain the supernatant for detection.

2. Detection of 8-Chloro-6-Hydroxyoctanoate Acid Ethyl Ester

Use GC to detect the content of 8-chloro-6-hydroxyoctanoic acid ethyl ester in the sample.

GC instrument model: Agilent 7890B.

TABLE 2

Enzyme activity and kinetic parameters of initial carbonyl reductase and its mutants

| Mutant | Specific activity (U/mg) | Number of conversions ($s^{-1}$) | Michaelis constant (mM) | Catalytic efficiency ($mM^{-1} \cdot s^{-1}$) | Relative catalytic efficiency |
|---|---|---|---|---|---|
| WT | 1.36 ± 0.05 | 4.7 ± 0.33 | 5.12 ± 0.87 | 0.92 | 1.00 |
| R129L/D210T | 45.41 ± 2.7 | 50.60 ± 1.49 | 1.74 ± 0.16 | 29.12 | 31.65 |
| R129L/D210T/S126A | 93.60 ± 1.49 | 69.46 ± 2.50 | 0.81 ± 0.11 | 85.95 | 93.42 |

Embodiment 3, Determination of Optimal Temperature and pH for Carbonyl Reductase CoCR 13 and its Mutants R129L/D210T/S126A (1) Optimal Temperature In the enzyme activity measurement system of Embodiment 2, except for pure enzyme solution, all other ingredients were incubated at the following temperatures (20° C.-50° C.) for 10 minutes and the enzyme activity was measured at the same temperature using a microplate reader.

Parameter setting: Chromatography column: DB-624UI (30×0.32 mm×1.8 µm); Maintain a column temperature of 200° C. for 5 minutes, then raise the temperature to 250° C. at a rate of 20° C./min and hold for 10 minutes; the temperature of injection port at 240° C.; constant pressure of 100 Kpa, split ratio of 25:1; FID: 260° C.

Determine the content of substrate 8-chloro-6-oxooctanoic acid ethyl ester and product 8-chloro-6-hydroxyoctanoic acid ethyl ester in the sample based on peak area. The gas chromatography results are shown in FIGS. 2, 3 and 4.

Figure 1:
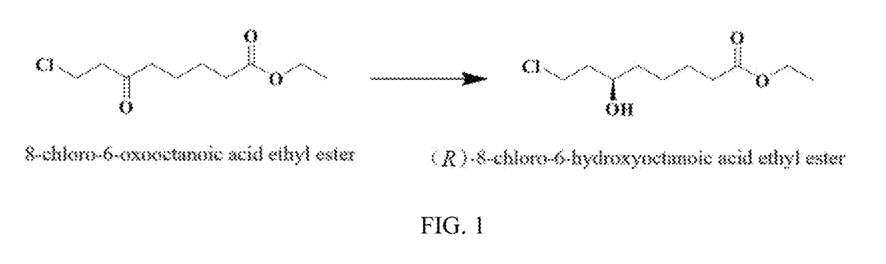
Figure 2:
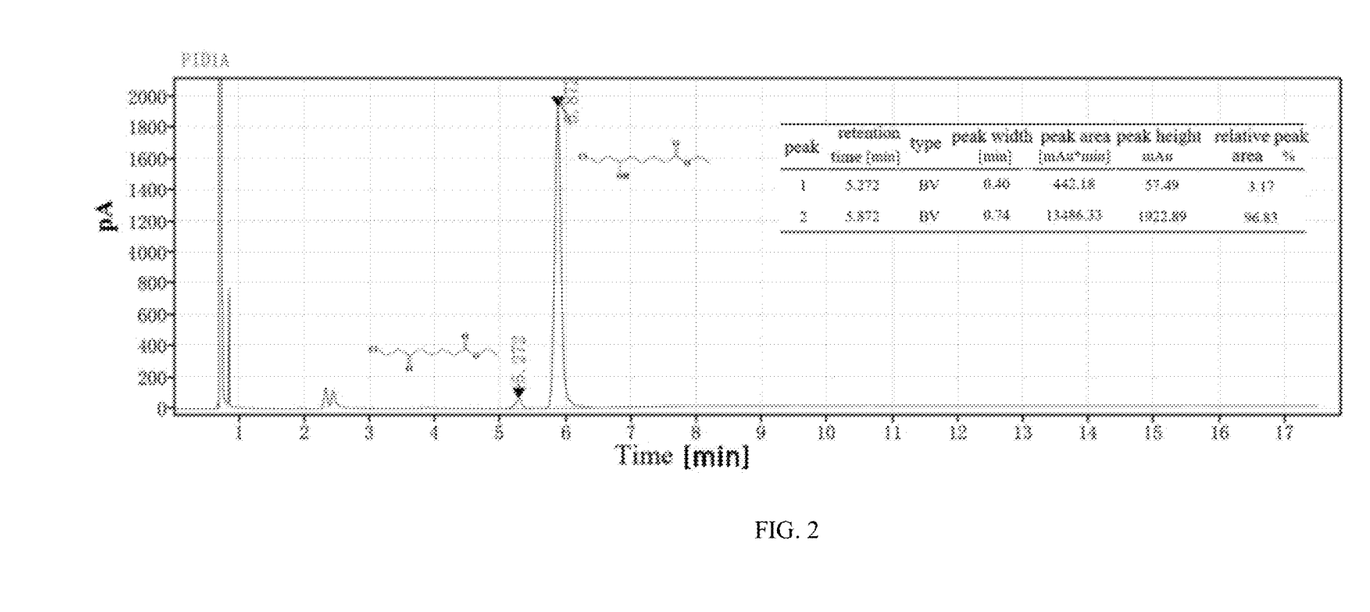
Figure 3:
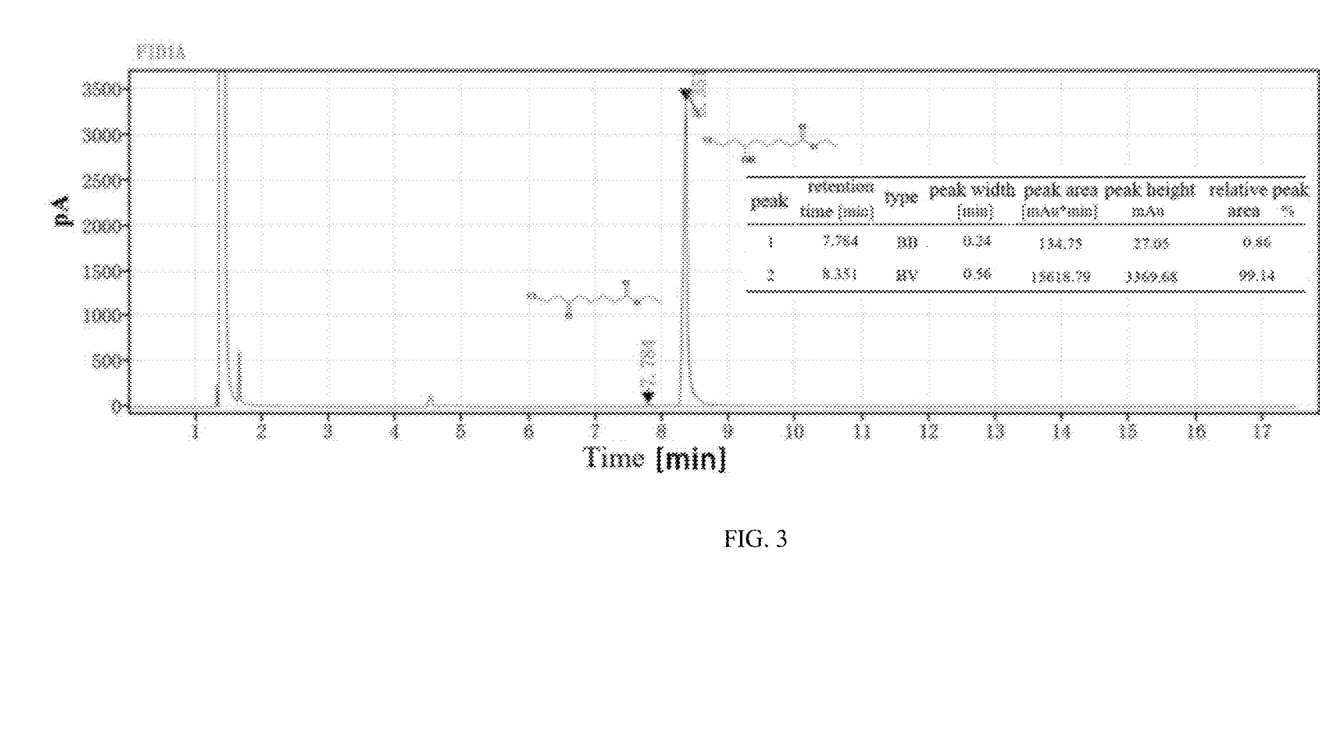
Figure 4:
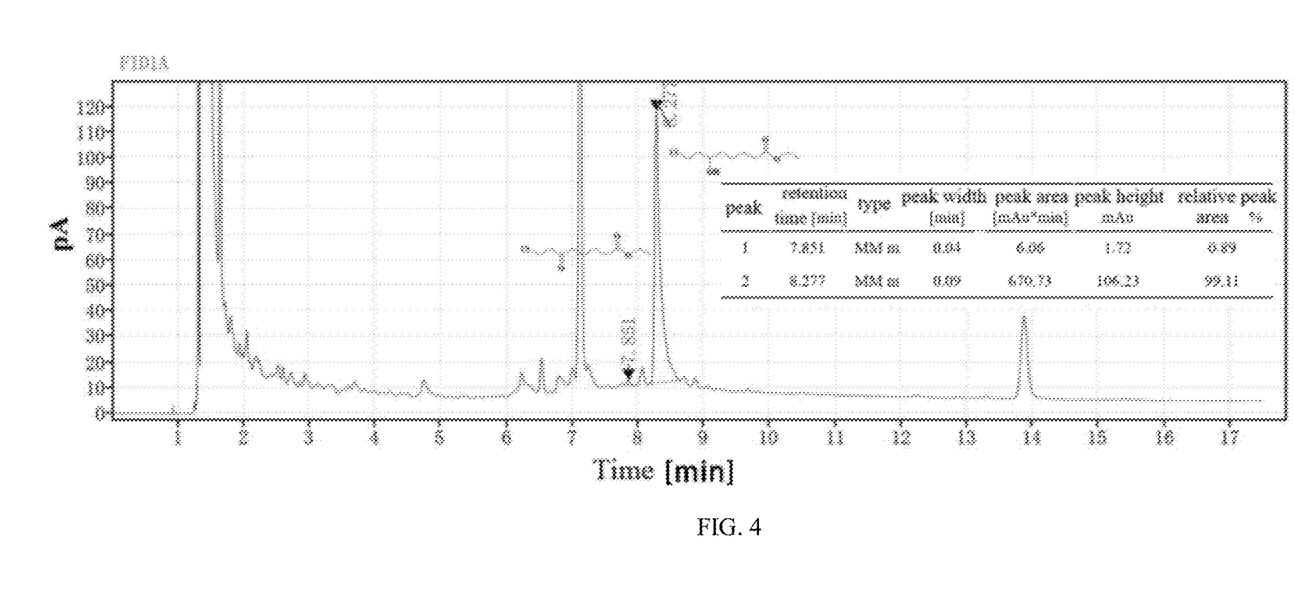

In the chromatograms corresponding to FIG. 2-FIG. 4, the peak information of the substrate 8-chloro-6-oxooctanoic acid ethyl ester and the product 8-chloro-6-hydroxyoctanoic acid ethyl ester are shown in Tables 3-5, respectively.

TABLE 3

Peak information of substrates and products corresponding to the chromatogram in FIG. 2

| Peak | Retention time (min) | Type | Peak width (min) | Peak area (mAu * min) | Peak height (mAu) | Relative peak area (%) |
|---|---|---|---|---|---|---|
| 1 | 5.272 | BV | 0.40 | 442.18 | 57.49 | 31.7 |
| 2 | 5.872 | BV | 0.74 | 13486.33 | 1922.89 | 96.83 |

TABLE 4

Peak information of substrates and products corresponding to the chromatogram in FIG. 3

| peak | retention time (min) | type | peak width (min) | peak area (mAu * min) | peak height (mAu) | relative peak area (%) |
|---|---|---|---|---|---|---|
| 1 | 7.784 | BB | 0.24 | 134.75 | 27.05 | 0.86 |
| 2 | 8.351 | BV | 0.56 | 15618.79 | 3369.68 | 99.14 |

TABLE 5

Peak information of substrates and products corresponding to the chromatogram in FIG. 4

| peak | retention time (min) | type | peak width (min) | peak area (mAu * min) | peak height (mAu) | relative peak area (%) |
|---|---|---|---|---|---|---|
| 1 | 7.851 | MMm | 0.04 | 6.06 | 1.72 | 0.89 |
| 2 | 8.277 | MMm | 0.09 | 670.73 | 106.23 | 99.11 |

Among them, FIG. 2 shows the gas chromatogram of the catalytic product of the carbonyl reductase mutant R129L/D210T in a 2 mL reaction, with a retention time of 5.872 min for 8-chloro-6-hydroxyoctanoic acid ethyl ester.

FIG. 3 shows the gas chromatogram of the catalytic product of the carbonyl reductase mutant R129L/D210T/S126A in a 2 mL reaction, with a retention time of 8.351 min for 8-chloro-6-hydroxyoctanoic acid ethyl ester.

FIG. 4 shows the gas chromatogram of the catalytic product of the carbonyl reductase mutant R129L/D210T/S126A in a 50 mL reaction, with a retention time of 8.277 min for 8-chloro-6-hydroxyoctanoic acid ethyl ester.

From FIG. 2-FIG. 4, it can be seen that the modified carbonyl reductase mutants of different types can successfully synthesize 8-chloro-6-hydroxyoctanoic acid ethyl ester.

In addition, HPLC was used to detect the chiral configuration of 8-chloro-6-hydroxyoctanoic acid ethyl ester in the sample.

HPLC instrument model: Thermo Fisher u3000.

Parameter setting: Chromatography column: Daicel IA (250×4.6 mm, 5 μm); wavelength 210 nm; mobile phase: n-hexane:isopropanol=95:5; flow rate of 0.8 mL/min.

Figure 5:
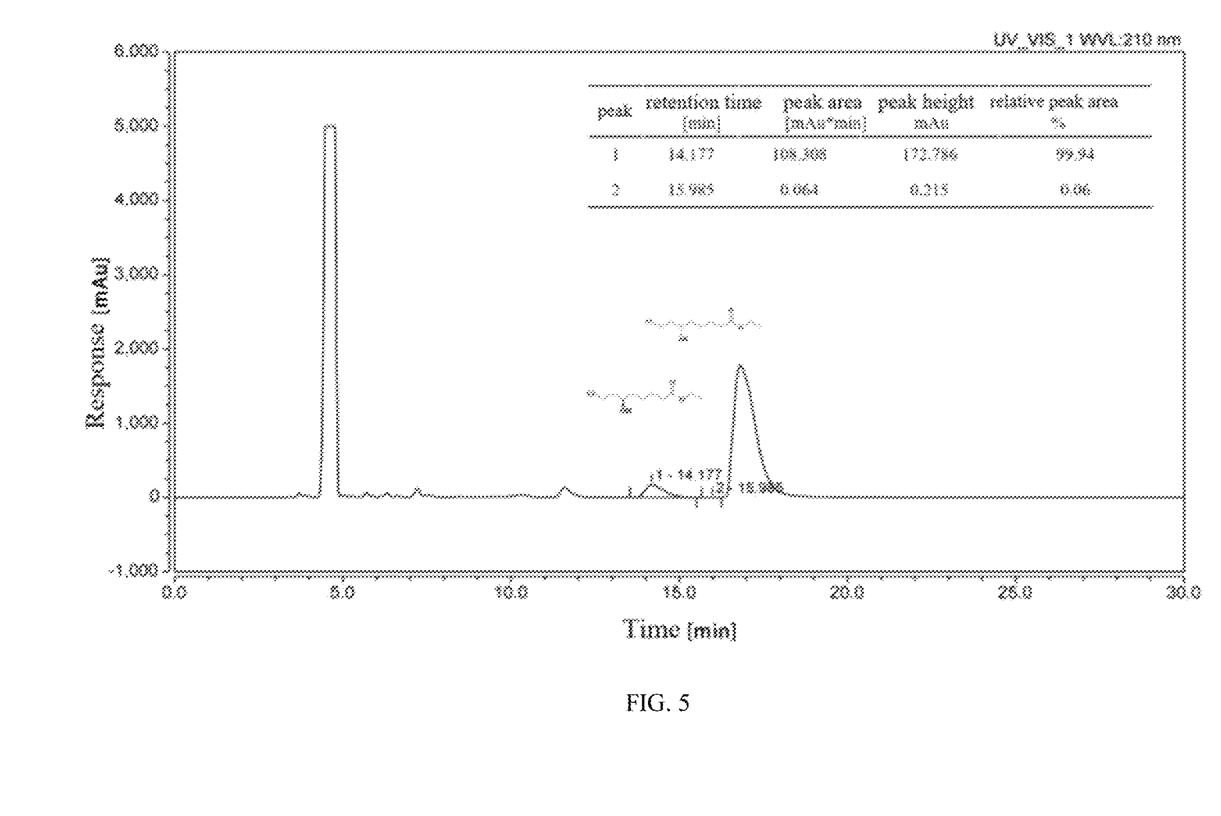
Figure 6:
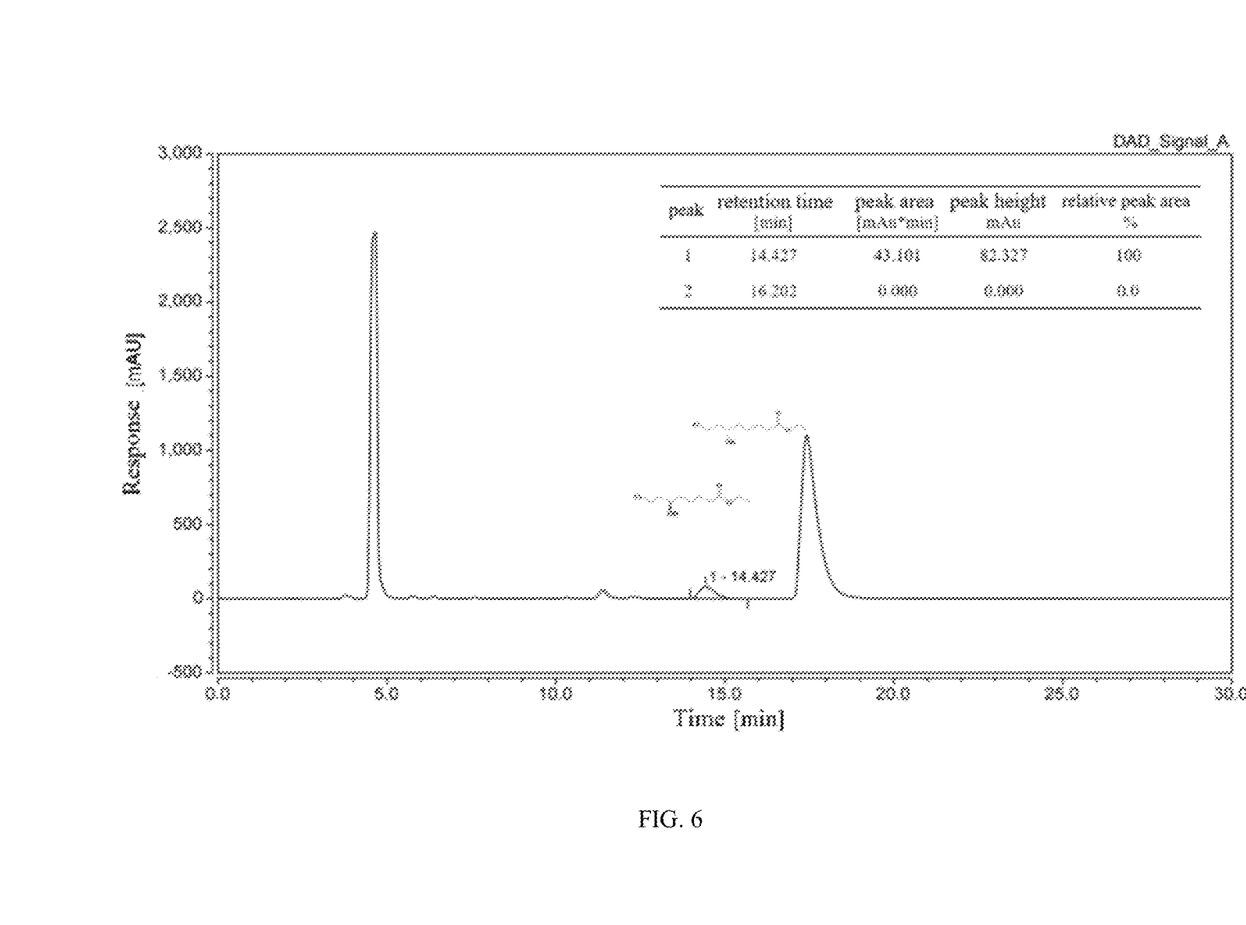
Figure 7:
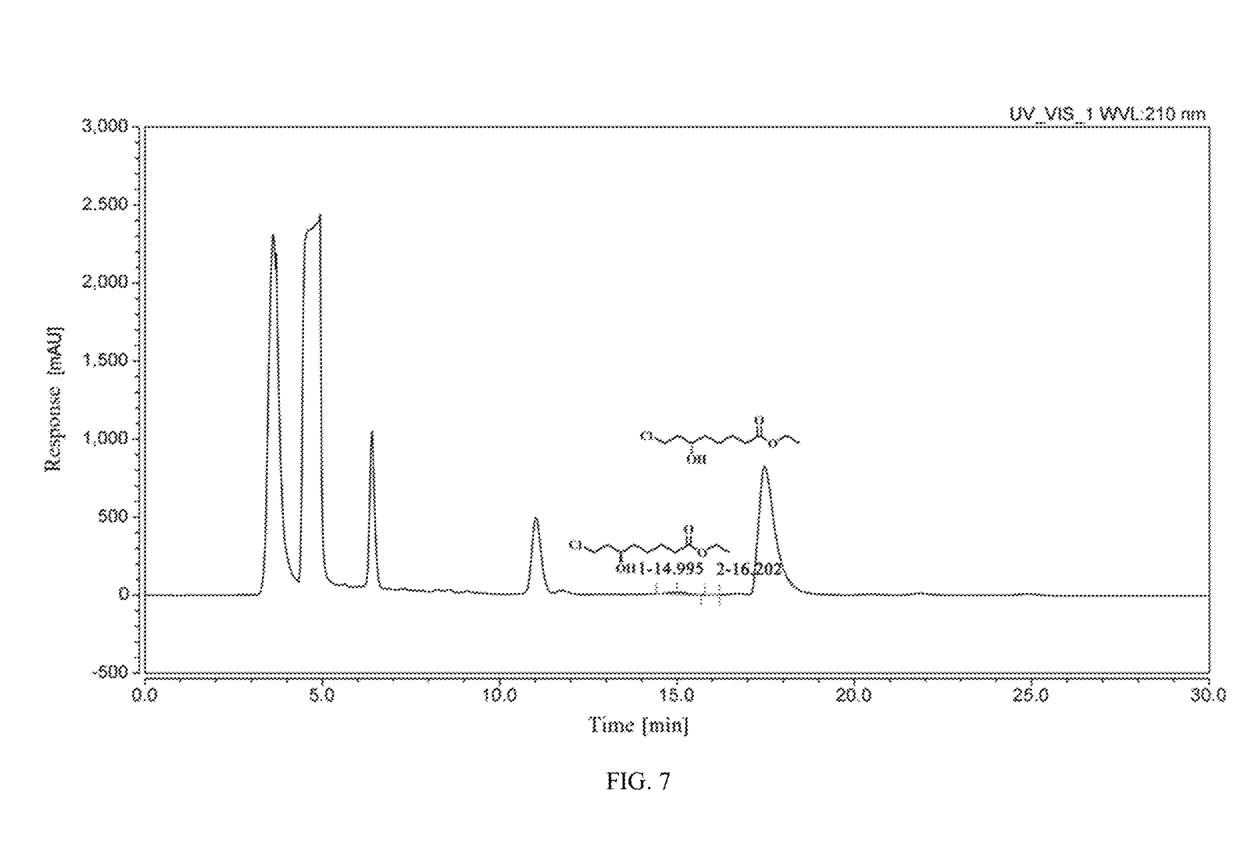

The content of different configurations of 8-chloro-6-hydroxyoctanoic acid ethyl ester in the sample was determined based on the peak area, and the high performance liquid chromatography results are shown in FIGS. 5, 6, and 7.

The peak information of different configurations of 8-chloro-6-hydroxyoctanoic acid ethyl ester in the chromatograms corresponding to FIG. 5-FIG. 7 are shown in Table 6 to Table 8.

TABLE 6

Peak information of substrates and products corresponding to chromatograms in FIG. 5

| peak | retention time (min) | peak area (mAu*min) | peak height (mAu) | relative peak area (%) |
|---|---|---|---|---|
| 1 | 14.177 | 108.308 | 172.786 | 99.94 |
| 2 | 15.985 | 0.064 | 0.215 | 0.06 |

TABLE 7

Peak information of substrates and products corresponding to chromatograms in FIG. 6

| peak | retention time (min) | peak area (mAu*min) | peak height (mAu) | relative peak area (%) |
|---|---|---|---|---|
| 1 | 14.427 | 43.101 | 82.327 | 100 |
| 2 | 16.202 | 0.000 | 0.000 | 0.0 |

TABLE 8

Peak information of substrates and products corresponding to chromatograms in FIG. 7

| peak | retention time (min) | peak area (mAu*min) | peak height (mAu) | relative peak area (%) |
|---|---|---|---|---|
| 1 | 14.995 | 8.379 | 13.878 | 99.76 |
| 2 | 16.202 | 0.020 | 0.000 | 0.24 |

Among them, FIG. 5 shows the high-performance liquid chromatography of products of different configurations synthesized by the carbonyl reductase mutant R129L/D210T in a 2 mL reaction. The retention time of (R)-8-chloro-6-hydroxyoctanoic acid ethyl ester is 14.177 min, and the retention time of (S)-8-chloro-6-hydroxyoctanoic acid ethyl ester is 15.985 min.

FIG. 6 shows the high-performance liquid chromatography of products of different configurations synthesized by the carbonyl reductase mutant R129L/D210T/S126A in a 2 mL reaction. The retention time of (R)-8-chloro-6-hydroxyoctanoic acid ethyl ester is 14.427 min, and the retention time of (S)-8-chloro-6-hydroxyoctanoic acid ethyl ester is 16.202 min.

FIG. 7 shows the high-performance liquid chromatography of products of different configurations synthesized by the carbonyl reductase mutant R129L/D210T/S126A in a 50 mL reaction. The retention time of (R)-8-chloro-6-hydroxyoctanoic acid ethyl ester is 14.995 min, and the retention time of (S)-8-chloro-6-hydroxyoctanoic acid ethyl ester is 16.202 min.

From FIG. 5-FIG. 7, it can be seen that the main configuration of 8-chloro-6-hydroxyoctanoic acid ethyl ester prepared using the carbonyl reductase mutant system prepared by the present disclosure is R-configuration, namely (R)-8-chloro-6-hydroxyoctanoic acid ethyl ester. The content of(S)-8-chloro-6-hydroxyoctanoic acid ethyl ester is extremely low, indicating that the carbonyl reductase mutant of the present disclosure can successfully catalyze the production of (R)-8-chloro-6-hydroxyoctanoic acid ethyl ester from the raw material 8-chloro-6-oxooctanoic acid ethyl ester.

What is claimed is:

1. A carbonyl reductase mutant, comprising the amino acid sequence as shown in SEQ ID NO: 3 or the amino acid sequence as shown in SEQ ID NO: 5.

2. A gene encoding the carbonyl reductase mutant according to claim 1.

3. The gene according to claim 2, wherein the gene encoding the carbonyl reductase mutant comprises the nucleotide sequence as shown in SEQ ID NO: 4 or the nucleotide sequence as shown in SEQ ID NO: 6.

4. A gene expression cassette, a vector, or a recombinant bacterium containing the gene as claimed in claim 2.

5. A preparation method of the carbonyl reductase mutant according to claim 1, comprising following steps: synthesizing a coding gene of an initial carbonyl reductase, conducting site directed mutagenesis of the coding gene of the initial carbonyl reductase to produce a gene encoding the carbonyl reductase mutant, constructing an expression vector containing the gene encoding the carbonyl reductase mutant, transforming a protein expression host bacterium with the expression vector, and inducing expression of the carbonyl reductase mutant in the host bacterium.

6. The method according to claim 5, wherein the gene encoding the carbonyl reductase mutant comprises the nucleotide sequence as shown in SEQ ID NO: 4 or the nucleotide sequence as shown in SEQ ID NO: 6.

* * * * *